United States Patent
Roemer et al.

(10) Patent No.: US 6,562,595 B2
(45) Date of Patent: May 13, 2003

(54) DOMINANT SELECTABLE MARKER FOR GENE TRANSFORMATION AND DISRUPTION IN YEASTS

(75) Inventors: Terry Roemer, Montreal (CA); Howard Bussey, Westmount (CA); John Davison, Montreal (CA)

(73) Assignee: McGill University, Montreal (CA)

( * ) Notice: Subject to any disclaimer, the term of this patent is extended or adjusted under 35 U.S.C. 154(b) by 55 days.

(21) Appl. No.: 09/785,669

(22) Filed: Feb. 16, 2001

(65) Prior Publication Data

US 2001/0031724 A1 Oct. 18, 2001

Related U.S. Application Data

(60) Provisional application No. 60/183,462, filed on Feb. 18, 2000.

(51) Int. Cl.$^7$ .................. C12N 15/00; C12N 15/09; C12P 21/06; C12Q 1/68; C07H 21/04
(52) U.S. Cl. .................. 435/69.1; 435/4; 435/6; 435/29; 435/252.3; 435/254.21; 435/254.22; 435/471; 435/483; 435/320.1; 536/23.1; 500/350
(58) Field of Search .................. 536/23.1; 435/69.1, 435/6, 4, 29, 320.1, 252.3, 471, 483, 254.21, 254.22; 500/350

(56) References Cited

PUBLICATIONS

Goldstein et al., Three new dominant drug resistance cassettes for gene disruption in saccharomyces cerevisiae, 1999, YEAST, vol. 15, 1541–1553.*

Alam et al., 1990, "Reporter Genes: Application to the Study of Mammalian Gene Transcription", Analytical Biochem. 188:245–254.

Austin et al., 1999, "Optimized vectors and selection for transformation of Neurospora crassa and Aspergillus nidulans to bleomycin and phleomycin resistance", Gene 93:157–162.

Baudin et al., 1993, "A Simple and Efficient Method for Direct Gene Deletion in Saccharomyces cerevisiae", Nucleic Acids Res. 21:3329–3330.

Bolivar et al., 1978, "Construction and Characterization of New Cloning Vehicles", Gene 4:121–136.

Douglas et al., 1994, "The Saccharomyces cerevisiae FKS1 (ETG1) gene encodes an integral membrane protein which is a subunit of 1,3–beta–D–glucan synthase", Proc Natl Acad Sci U S A. 91(26):12907–11.

Fonzi and Irwin, 1992, "Isogenic strain construction and gene mapping in Candida albicans", Genetics 134(3):717–728.

Giaever et al., 1999, "Genomic profiling of drug sensitivities via induced haploinsufficiency", Nat Genet. 21(3):278–283.

Gietz and Sugino, 1988, "New yeast–Escherichia coli shuttle vectors constructed with in vitro mutagenized yeast genes lacking six–base pair restriction sites", Gene. Dec. 30, 1988; 74(2):527–534.

Gold et al., 1994, "Three selectable markers for transformation of Ustilago maydis", Gene 142(2):225–230.

Jimenez and Davies, 1980, "Expression of a transposable antibiotic resistance element in Saccharomyces", Nature.287(5785):869–871.

Joshi et al., 1995, "The gene encoding streptothricin acetyltransferase (sat) as a selectable marker for Leishmania expression vectors", Gene. 156(1):145–149.

Karreman et al., 1998, "New positive/negative selectable markers for mammalian cells on the basis of Blasticidin deaminase–thymidine kinase fusions", Nucleic Acids Res. 26(10):2508–2510.

Krugel et al., 1993, "Sequence and transcriptional analysis of the nourseothricin acetyltransferase–encoding gene nat1 from Streptomyces noursei", Gene 127:127–131.

Pla et al., 1996, Understanding Candida albicans at the molecular level. Yeast. Dec. 1996;12(16):1677–1702.

Stoldt et al, 1997, "Efg1p, an essential regulator of morphogenesis of the human pathogen Candida albicans, is a member of a conserved class of bHLH proteins regulating morphogenetic processes in fungi", EMBO J. 16(8):1982–1991.

Wach et al., 1994, "New heterologous modules for classical or PCR–based gene disruptions in Saccharomyces cerevisiae", Yeast. 10(13):1793–1808.

Webster et al., 1983, "Direct selection of Saccharomyces cerevisiae resistant to the antibiotic G418 following transformation with a DNA vector carrying the kanamycin–resistance gene of Tn903", Gene. 26(2–3):243–252.

Zahringer et al., 1993, "Nourseothricin (streptothricin) inactivated by a plasmid pIE636 encoded acetyl transferase of Escherichia coli: location of the acetyl group", FEMS Microbiol Lett. 110(3):331–334.

* cited by examiner

Primary Examiner—David Guzo
Assistant Examiner—Gerald G. Leffers, Jr.
(74) Attorney, Agent, or Firm—Pennie & Edmonds LLP

(57) ABSTRACT

The present invention provides a novel dominant selectable marker system in yeast that is based on an aminoglycoside, nourseothricin (NST). This compound possesses a powerful antifungal activity against Candida albicans and S. cerevisiae. The invention provides a cognate drug resistance marker for use in gene transformation and disruption experimentation in Candida albicans and Saccharomyces cerevisiae. In particular, the invention presents: 1) direct utility for gene manipulations in both clinically and experimentally relevant strains regardless of genotype and without affecting growth rate, or hyphal formation; and 2) applicability to antifungal drug discovery, including target validation and various forms of drug screening assays.

19 Claims, 5 Drawing Sheets

SEQ ID NO: 1

Figure 1:
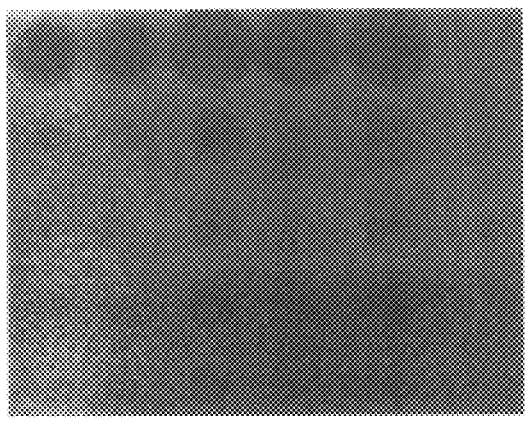
Figure 1:
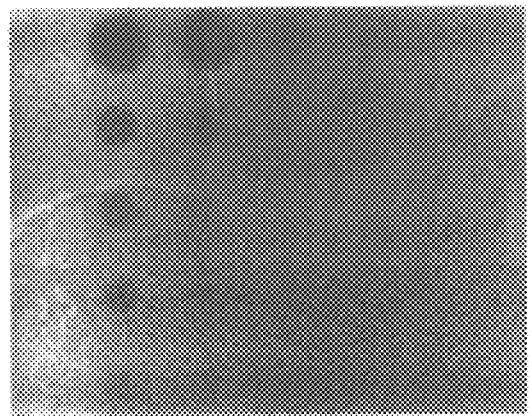

```
  1  atgaagattt cggtgatccc tgagcaggtg gcggaaacat tggatgctga
 61  gaaccatttc attgttcgtg aagtgttcga tgtgcaccta tccgaccaag
111  gctttgaact atctaccaga agtgtgagcc cctaccggaa ggattacatc
161  tcggatgatg actctgatga agactctgct tgctatggcg cattcatcga
211  ccaagagctt gtcgggaaga ttgaactcaa ctcaacatgg aacgatctag
261  cctctatcga acacattgtt gtgtcgcaca cgcaccgagg caaggagtc
311  gcgcacagtc tcatcgaatt tgcgaaaaag tgggcactaa gcagacagct
361  ccttggcata cgattagaga cacaaacgaa caatgtacct gcctgcaatt
411  tgtacgcaaa atgtggcttt actctcggcg gcattgacct tttcacgtat
461  aaaactagac ctcaagtctc gaacgaaaca gcgatgtact ggtactggtt
511  ctcgggagca caggatgacg cctaa
```

FIG.5A

SEQ ID NO:2

```
  1  mkisvipeqv aetldaenhf ivrevfdvhl sdqgfelstr svspyrkdyi
 61  sdddsdedsa cygafidqel vgkielnstw ndlasiehiv vshthrgkgv
111  ahsliefakk walsrqllgi rletqtnnvp acnlyakcgf tlggidlfty
161  ktrpqvsnet amywywfsga qdda
```

FIG.5B

DOMINANT SELECTABLE MARKER FOR GENE TRANSFORMATION AND DISRUPTION IN YEASTS

This application claims priority to the U.S. provisional application No. 60/183,462, filed Feb. 18, 2000, which is incorporated herein by reference in its entirety.

1. INTRODUCTION

This invention relates to the discovery of nourseothricin (NST) drug sensitivity in the pathogenic yeast, *Candida albicans* and in *Saccharomyces cerevisiae*. In particular, the present invention relates to a cognate drug resistance marker system for use in gene transformation and disruption experimentation. Specifically, the present invention provides a modified nourseothricin/streptothricin resistance gene, SAT, for expression in *C. albicans*. The present invention also provides a cell, nucleic acid molecule, and vector comprising the modified SAT1 nucleic acid sequence. The present invention further provides a SAT expression module for gene knock-outs.

2. BACKGROUND OF THE INVENTION

Opportunistic fungi are a rapidly emerging class of microbial pathogens causing systemic fungal infection or "mycosis" in patients immunocompromised either by illness (e.g., AIDS) or standard medical treatment (e.g., organ transplants, chemotherapy, radiation therapy). Candida spp. rank as the predominant genus of such fungal pathogens. In recent years, rapid and reliable diagnosis of fungal infection has advanced primarily through the application of molecular biological techniques. Understanding the pathogenesis of this organism, from which novel treatment strategies will develop, is also dependent on improved techniques in molecular genetics.

The recent commitment by the Stanford Sequence Center to sequence the entire *C. albicans* yeast genome will accelerate our understanding in both the biology and eventual treatment of candidiasis. The DNA sequence resulting from this enterprise however offers only a prediction towards potential pathogenesis pathway(s) and antifungal targets. Maximum information gained from this effort requires experimentation. The ability to study the role of any particular gene, both by abolishing its function through gene disruption experiments, as well as overproducing its gene product through transformation experiments, directly tests the predictions made by bioinformatic analysis. As *C. albicans* is an imperfect fungus which lacks a sexual cycle and is fixed in the diploid state, gene disruption experiments are more cumbersome, requiring replacement of both alleles of the target gene before an examination of its null phenotype be determined. To this end, improved DNA methodologies are required for experimentation in *C. albicans*.

Currently, auxotrophic markers are employed to select for precise genetic alterations in *C. albicans*. Auxotrophic markers are recessive mutations, usually in biosynthetic genes, which can be complemented by either supplementing the yeast strain with the desired requirement (e.g., uridine) or by transformation of the wild type gene. A number of non-reverting, auxotrophic mutations, to which the complementing wild type gene has been cloned, are available for genetic manipulations in *C. albicans* (Pla et al., 1996 Yeast 12:1677–1702). CAI4, the standard *C. albicans* strain employed by researchers, contains a single auxotrophic marker—a homozygous null mutation in the CaURA3 gene.

The utility of this strain stems largely from a "URA-blaster" gene disruption procedure developed for *C. albicans* by Fonzi and Irwin (1993 Genetics 134:717–728) which utilizes a CaURA3 gene flanked by direct repeats of the *Salmonella typhimurium* HisG gene. This Ura-blaster cassette is used to replace part of the target gene in vitro. The resulting disruption cassette is then transformed into CAI4, whereby through homologous recombination, Ura+ transformants harboring a heterozygous mutation for the target gene are selected. Counterselection on 5-fluoroorotic acid (5-FOA), relying on intrachromosomal recombination between HisG repeats, excises the CaURA3 gene, leaving a single copy of the HisG sequence within the target gene, and allowing reuse of the auxotrophic marker-based disruption cassette for disruption of the target gene's second allele.

Despite a reliance on auxotrophic markers to select for successful DNA transformation or gene disruption, this dependency comes with significant limitations. Firstly, analysis is restricted to the genetic background to which the auxotrophic mutation has been introduced and the complementing gene available. This severely restricts genetic analyses of clinical isolates which lack auxotrophic markers. Alternatively, a specially constructed strain containing the appropriate auxotrophic marker must first be constructed, a procedure which is both time consuming and problematic. A second common problem associated with auxotrophic markers is the limited number of stable mutations constructed in a particular strain background. As outlined above, CAI4, the most widespread *C. albicans* strain used for genetic manipulation, maintains only a single auxotophic marker. Although, the URA3 marker can be reused in gene disruption experiments, this process has significant drawbacks, and more sophisticated manipulations (for example, the selection and stable maintenance of a second gene) are difficult. Auxotrophic mutations also potentially affect physiological processes such as pathogenicity, rendering the strain inappropriate for virulence studies (Pla et al., 1996, Yeast 12:1677–1702). Therefore, a strain maintaining multiple auxotrophic mutations must be complemented for each mutation in order to perform virulence studies, and even under such conditions, issues of haplo-insufficiency add further complexity to the utility of such a multiply-marked *C. albicans* strain. In theory, the Ura-Blaster method overcomes this issue of limited auxotrophic markers for multiple gene disruptions by the ability to reuse the Ura3 marker. In practice however, additional problems develop, most notably the introduction of extragenic mutations which accumulate through successive counterselections on 5-FOA; which itself is a mutagenic compound. Repeated use of the procedure, for example in the construction of a double homozygote strain, may add multiple extragenic mutations; any of which can potentially contribute to phenotype(s) unlinked to either of the disrupted loci and consequently complicate interpretation of the result. Another problem common to auxotrophic mutations is the altered growth rate they impart, in addition to their potential for contributing a further variable into phenotypic analyses. For example, despite the addition of supplementary Uridine to hyphal-inducing media, CAI4 neither forms as extensive hyphae, nor switches from the budding form to hyphal form as rapidly as its Ura3+ parent strain, SC5314.

Historically auxotrophic markers have contributed tremendously to basic research of the bakers' yeast, *Saccharomyces cerevisiae*. However, a clear trend towards the use of a dominant drug selectable marker has developed, principally by an international consortium of researchers participating in the *S. cerevisiae* genome knock out project. To this end, a single dominant selectable marker has been constructed, comprising the *E. coli*-derived kanamycin resistance gene, Kan$^R$, flanked by *Ashbya gossypii* TEF3 promoter and terminator regulatory sequence (Wach et al., 1994, Yeast 10:1793–1808; Jimenez and Davies, 1980, Nature 287:869–871). This KanMX module is expressed in *S. cerevisiae* and confers resistance to the Kanamycin-related aminoglycoside, geneticin, allowing selection for the desired strain when plated in the presence of the drug after transformation. The use of this KanMX module in place of auxotrophic markers solves many of the above discussed problems associated with their use. Genetic manipulations employing this dominant selectable marker can now be carried out directly in any *S. cerevisiae* strain. Studies comparing Kan$^r$-marked versus wild type strains incubated together in a chemostat reveal no detectable difference in growth rate associated with the maintenance of the KanMX module. Moreover, no indirect effects on physiological, developmental, or morphological processes are detected. Because the KanMX disruption module is completely heterologous, the efficiency of proper integration into the target locus is also greatly improved, minimizing the effort to identify the correctly disrupted strain. Thus, the greatest drawback appears to be the limited number of dominant selectable markers which exist for experimental manipulation in *S. cerevisiae*.

3. SUMMARY OF THE INVENTION

The present invention provides a novel dominant selectable marker system in fungi that is based on the nucleoside-like antibiotic, nourseothricin (NST). This compound possesses a powerful antifungal activity against *C. albicans* as well as *S. cerevisiae*. In particular, the present invention exploits the discovery of NST sensitivity in the pathogenic yeast, *C. albicans*, which leads to the development of a drug resistance marker useful in gene transformation and gene disruption experiments. The dominant selectable marker system of the invention facilitates: 1) gene manipulations in both clinically and experimentally relevant strains regardless of genotype and without affecting growth rate, or hyphal formation; and 2) antifungal drug discovery, including target validation and various forms of drug screening assays.

As used herein, SAT1 refers to the naturally occurring bacterial acetyltransferase genes and protein product and NAT1 refers to the naturally occurring nourseothricin N-acetyltransferase from *Streptomyces noursei*. Modified SAT1 and modified NAT1 refer to the modified SAT1 and NAT1 nucleic acid sequences, respectively, of the present invention used in fungus such as *C. albicans*. SAT and NAT refer to homologs of SAT1 and NAT1.

The present invention provides a genetically modified nourseothricin/streptothricin resistance gene derived originally from the *E. coli* SAT1 gene, for expression in *C. albicans*. Specifically, the present invention provides a nucleic acid molecule comprising (a) the nucleotide sequence of SEQ ID NO:1; or (b) a nucleotide sequence that encodes the amino acid sequence of SEQ ID NO:2 when the nucleotide sequence is translated according to the codon usage of *Candida albicans*.

The present invention further provides a number of SAT expression modules, comprising promoter and terminator sequences from *C. albicans* genes. In one embodiment, the promoter and termination sequences are from *C. albicans* genes, which include but are not limited to, CaACT1, and CaPCK1.

These modules have been constructed and shown to serve as dominant nourseothricin-resistance (NST$^R$) gene markers for transformation of a fungal vector in *C. albicans*. Maintenance of the SAT expression module shows no deleterious effect on growth rate or hyphal formation. Accordingly, the present invention provides a cell, nucleic acid molecule, and vector comprising the modified SAT1 nucleic acid sequence.

The present invention also provides a SAT expression module for Polymerase Chain Reaction (PCR) based gene knock-outs which has been used to disrupt an allele of *C. albicans* genes CaKRE1, CaWSC4, and CaYHR036w. In addition, the present invention further provides the use of the SAT1 gene as the primary selectable marker or as a second dominant-selectable marker suitable for gene disruption in *S. cerevisiae*.

The present invention provides a kit which comprises an expression vector that expresses streptothricin acetyltransferase in yeast, such as *C. albicans*.

The present invention provides a strain of *C. albicans* that produces the SAT1 protein. The present invention provides a strain of yeast which is resistant to NST. Accordingly, the present invention provides a method of culturing yeast cells in the presence of NST, said method comprising introducing a nucleic acid molecule comprising a nucleotide sequence encoding a SAT1 protein or a nucleic acid molecule comprising a modified SAT1 in the yeast cells, and culturing the yeast cells such that SAT1 protein is expressed in the yeast cells.

The present invention further provides a method of using the modified SAT1 gene as a resistance marker for transformation and/or disruption of genes in *C. albicans*.

The present invention also provides a method of using the yeast strains comprising modified SAT1 nucleotide sequence. Specifically, the present invention provides a method for introducing recombinant DNA comprising a modified SAT1 gene into *C. albicans* for obtaining stable transformants.

The present invention provides a method of identifying yeast cells comprising the modified SAT1 nucleic acid of the invention, which method comprises introducing the modified SAT1 nucleic acid of the invention into the yeast cells and culturing the yeast cells in the presence of nourseothricin for a time sufficient for the expression of the SAT1 protein such that yeast cells that contain the nucleic acid molecule grow faster than yeast cells that do not contain or express the nucleic acid molecule, thereby allowing the yeast cells that contain the nucleic acid molecule to be identified. The yeast cells that do not contain the nucleic acid molecule grow slowly, if at all, or they may be killed by the nourseothricin.

The present invention provides a method for enriching yeast cells comprising a first nucleic acid molecule, which method comprises introducing a mixture of the modified SAT1 nucleic acid of the invention and the first nucleic acid molecule into the yeast cells and culturing the yeast cells in the presence of nourseothricin for a time sufficient for the expression of SAT1 such that yeast cells that contain the nucleic acid molecule grow faster than yeast cells that do not contain or express the nucleic acid molecule, thereby allowing the yeast cells that contain the modified SAT1 nucleic acid molecule to be identified and recovering the yeast cells that comprise the modified SAT1 nucleic acid molecule wherein the recovered yeast cells are enriched for yeast cells that comprise the first nucleic acid molecule. The yeast cells that do not contain the nucleic acid molecule grow slowly, if at all, or they may be killed by the nourseothricin.

The present invention also provide the use of NST as a fungicide, for controlling the growth of or killing fungi, in particular pathogenic fungi such as *C. albicans*. NST can be used for protecting objects from contamination by such fungi.

The present invention also provides a method of inhibiting the growth of *Candida albicans* cells comprising contacting *Candida albicans* cells with a composition comprising an effective amount of nourseothricin.

The present invention also provides a method of inhibiting the growth of *Saccharomyces cerevisiae* cells comprising contacting *Saccharomyces cerevisiae* cells with a composition comprising an effective amount of nourseothricin.

The present invention also provides a method of preventing or reducing contamination of an object by a fungus comprising contacting the object with a composition comprising an effective amount of nourseothricin.

The present invention also provides a method of preventing or reducing formation on a surface of a biofilm comprising *Candida albicans*, said method comprising contacting the surface with a composition comprising an effective amount of nourseothricin.

The present invention provides the method of treatment of a disease in a subject caused by an infection by a pathogenic fungus which comprises administering to the subject a pharmaceutical composition comprising a pharmaceutically acceptable carrier and NST.

The present invention provides a culture medium suitable for growth of *C. albicans* and *S. cerevisiae* comprising nourseothricin.

4. BRIEF DESCRIPTION OF FIGURES

FIG. 1 shows a schematic diagram that *C. albicans* and *S. cerevisiae* are sensitive to nourseothricin. Confluent plates of either *S. cerevisiae* diploid strain SEY6210 (left panel) or *C. albicans* strain SC5314 (right panel) were spotted with 5 µl of destomycin (DSM), blasticidin (BSN), nourseothricin (NST), geneticin (G418), zeocin (ZEO), and puromycin (PUR) using concentrations of 10 mg/ml, 1 mg/ml, 0.5 mg/ml, 0.25 mg/ml, 0.125 mg/ml, and 0.06 mg/ml (top to bottom). Zones of inhibition were examined after overnight growth; clear halos indicate antifungal activity;

FIG. 2, Panels A-D, shows a schematic drawing of SAT dominant selectable marker modules. A) ASTHMA comprises a 1.0 kb of CaACT1 promoter (ACT1P) and 0.65 kb CaACT1 termination (ACT1T) sequence flanking the SAT open reading frame; B) PSMP comprises a 1.43 kb of CaPCK1 promoter (I) and 0.67 kb of CaPCK1 termination (PCK1T) sequence flanking SAT; and C) ASMP is a hybrid module containing the CaACT1 promoter and CaPCK1 terminator for SAT expression. All *C. albicans* subcloning fragments are derived from PCR amplification of SC5314 genomic DNA. Unique restriction sites (BglII (Bg), PstI (P), HindIII (H), NcoI (N), DraI (D), and ScaI (Sc)) were added to facilitate subclonings. All SAT expression modules for *C. albicans* expression are mutagenized to change the codon for LEU147 from CTG to CTT. D) SATMX4 was constructed by first removing a ScaI site within the KANMX4 plasmid backbone by mutagenesis. The KanR gene was removed by NcoI digestion followed by T4 DNA polymerase fill in, and later ScaI digestion. The nucleotide sequence encoding SAT1 was ligated into this vector as a ScaI/DraI-containing PCR product. Restriction sites lost in subclonings are shown in italics;

FIG. 3 (Panels A–B) shows a schematic diagram that both ASTHMA and PSMP A. transformants confer nourseothricin resistance in *C. albicans*. ASTHMA, PSMP, and vector alone (lacking either SAT expression module) plasmids were transformed into CAI4 and directly selected on YPD-drug supplemented plates (400 µg/ml) prior to being restreaked onto a YPD plate containing 400 µg/ml nourseothricin. A) Six independent ASTHMA transformants, as well as the negative controls CAI4, containing pRC18, and the parent strain, SC5314 are shown after two days growth at 30° C. on YPD plates containing 400 µg/ml NST. B) Four independent PSMP transformants, as well as the negative controls, CAI4 maintaining pRC18, and SC5314, grown on YPD (left plate), and either derepressing conditions (1% Casamino acid+300 µg/ml NST, center plate), or repressing conditions (YPD+300 µg/ml NST, right plate) for PCK1 promoter-dependent expression of SAT. Plates were incubated two days at 30° C.; and FIG. 4 (Panels A–B) shows a schematic diagram that SAT functions as a dominant selectable marker in a PCR-based gene disruption of FKS1 in *S. cerevisiae*. Tetrad dissection of a representative FKS1/fks1D::SAT heterozygote strain grown on YPD and replica plated onto YPD+300 µg/ml NST demonstrates slow growth phenotype of fks1D alleles cosegregates with SAT-dependent NST resistance.

FIGS. 5(A)–(B) show the sequences of SAT. (A) nucleic acid sequence of the open reading frame of a modified SAT1 (SEQ ID NO: 1). (B) amino acid sequence of SAT1 (SEQ ID NO: 2).

5. DETAILED DESCRIPTION OF THE INVENTION

The present invention relates to the development of nourseothricin (NST) as a dominant selectable marker useful for genetic manipulation of fungi. In particular, the present invention provides the use of NST sensitivity in *S. cerevisiae*, and in the pathogenic yeast, *C. albicans*. NST was demonstrated to possess potent fungicidal activity which allowed the development of a dominant drug-based selectable marker system for gene transformation and gene disruption experiments in *C. albicans* and *S. cerevisiae*.

5.1 Drug Sensitivity in Yeast

To explore the possibility of developing a dominant selectable marker for *C. albicans*, geneticin, the aminoglycoside used in dominant selection studies in *S. cerevisiae* was initially examined for antifungal activity in *C. albicans* (FIG. 1). Geneticin failed to show significant fungicidal activity against *C. albicans* strain SC5314 by halo assay at concentrations several-fold higher than typically used in selection experiments in *S. cerevisiae*. Nourseothricin was found to display potent antifungal activity towards *S. cerevisiae* strain SEY6210, at concentration dramatically below that at which geneticin acts (FIG. 1). When a number of alternative commercially available antibiotics including zeocin, destomycin, nourseothricin, blasticidin, and puromycin were tested for antifungal activity, the present inventors discovered that *C. albicans* was sensitive to nourseothricin at a concentration of about 200 µg/ml. This concentration is comparable to that which geneticin is used in *S. cerevisiae* transformations. *C. albicans* was also found to be sensitive to blasticidin. However, nourseothricin was dramatically more effective on rich media such as YPD plates which has a high salt content than minimal media-based YNB plates. (Webster et al., 1983, Gene 26:243–252).

Accordingly, the present invention provides a method of using NST as a fungicide to control the growth of and/or to kill yeasts, such as *S. cerevisiae*, and pathogenic yeast, such as *C. albicans*. In a preferred embodiment, the method uses about 200 µg/ml of NST. For in vitro application, it is preferred that a culture medium that has high salt content, such as YPD medium, be employed when NST is used. The present invention also encompasses the use of NST as an agent to prevent contamination of objects by fungi.

The present invention also provides a method of preventing or reducing formation on a surface of a biofilm comprising *Candida albicans*, said method comprising contacting the surface with a composition comprising an effective amount of nourseothricin. For example, biofilm can be prevented from being formed on the surface of medical devices, such as but not limited to stents, catheters and other implantable devices.

In another embodiment, the invention provides a method using blasticidin to regulate the growth of yeasts, such as *C. albicans*.

The present inventors also compared the sensitivity of NST to geneticin in *S. cerevisiae*. Despite substantial structural similarity between geneticin and nourseothricin, a *S. cerevisiae* strain maintaining the geneticin resistance gene, $Kan^R$ failed to confer resistance to nourseothricin. The result suggested that an alternative resistance gene is necessary to serve as a dominant selectable marker. Therefore, nourseothricin was demonstrated to possess potent fungicidal activity and is suitable for the development of a drug-based selectable marker for transformation in yeasts.

5.2 The Modified SAT1 Gene

Bacterial resistance to nourseothricin is mediated by acetylation of the bacterial acetyltransferases SAT1. Consistent with the observed sensitivity to NST, genome database searches using the bacterial acetyltransferases, streptothricin acetyltransferase, SAT1, and *streptomyces noursei*'s nourseothricin acetyltransferase, NAT1, failed to detect significant sequence homology to *S. cerevisiae* or available *C. albicans* sequences.

To test whether acetyltransferase activity could impart *C. albicans* resistance to nourseothricin, the *E. coli* SAT1 (streptothricin acetyltransferase 1) gene, which confers resistance to the drug was engineered for expression in *C. albicans*. However, *C. albicans* utilizes an altered genetic code, in which the standard (CTG) codon for leucine is translated as serine. Accurate expression of the bacterial SAT1 gene in *C. albicans* is made possible by engineering the gene so that its DNA sequence is altered such that the DNA sequence is translated according to the codon usage of *C. albicans*. Accordingly, a G to T mutagenesis was performed on the CTG codon present in the *E. coli* SAT1 gene which encodes a leucine at amino acid position 147 (nucleotide position 441) to CTT. Accordingly, the invention provides a modified SAT1 gene (SEQ ID NO:1). In a specific embodiment, the modified SAT1 gene is CaSAT1. The nucleic acid molecules of the invention thus comprises the nucleotide sequence that encodes *E. coli* SAT1 (SEQ ID NO:2) that has been modified to encode a functional SAT1 enzyme in *C. albicans*. Accordingly, the nucleic acid molecule of the invention comprises a modified SAT1 gene of *E. coli*, having a nucleotide sequence in which the nucleotide at 441 is thymine (SEQ ID NO:1). In the present invention, subcloning fragments are derived from PCR amplification SC5314 genomic DNA, as described below. Further, unique restriction sites BglII, PstI, HindIII, NcoI, DraI and ScaI were added to facilitate subcloning. The presence of the *E. coli* SAT1 gene product within *C. albicans* allows acetylation of the drug rendering it nontoxic and permitting the strain to grow in the presence of nourseothricin at a concentration of 200 micrograms per milliliter.

The invention also provides the use of other streptothricin acetyltransferase (SAT) or nourseothricin acetyltransferase (NAT) proteins and the genes encoding therefor as a dominant selectable marker in yeasts, such as *S. cerevisiae* or *C. albicans*. The homologous genes encoding the enzyme can be identified by computer database searches using the SAT1 or NAT1 sequence, and such homologs, SAT or NAT, can be isolated by cloning techniques well known in the art.

One of skill in the art will recognize that successful expression of a bacterial acetyetransferase protein in *C. albicans* may be obtained by utilizing an altered genetic code. Accordingly, the present invention provides modified nucleotide sequences that encode a functional streptothricin or nourseothricin acetyltransferase enzyme derived from other organisms, for example, *Bacillus cereus*. The present invention also encompasses modified acetyletransferases including NAT1 which conforms to the codon usage of *C. albicans* and thus encodes a functional nourseothricin acetyltransferase 1 in *C. albicans*.

The present invention also provides the use of conservatively modified variation of nucleic acid sequence encoding SAT1. Conservatively modified variations of a particular nucleic acid sequence refers to nucleic acids that encode identical or essentially identical amino acid sequences. Due to the degeneracy of the genetic code, a large number of functionally identical nucleic acids encode a single polypeptide sequence. When a nucleic acid sequence is changed at one or more positions with no corresponding change in the amino acid sequence which it encodes, that mutation is called a "silent mutation". Thus, one species of a conservatively modified variation according to this invention is a silent mutation. Accordingly, the present invention also provides every possible silent mutation or variation that encodes a SAT1 polypeptide, in particular, changes that conform to the codon usage of *C. albicans*.

Furthermore, one of skill in the art will recognize that individual substitutions, deletions, additions and the like, which alter, add or delete a single amino acid or a small percentage of amino acids (less than 5%, more typically less than 1%) in an encoded sequence are conservatively modified variations where the alterations result in the substitution of one amino acid with a chemically similar amino acid. Conservative substitution tables providing functionally similar amino acids are well known in the art. Accordingly, the present invention also provides a nucleic acid molecule that encodes a conservatively modified SAT1 enzyme.

In another embodiment, where alteration of function is desired, one or more additions, deletions or non-conservative alterations can produce altered SAT1 gene products, including SAT1 gene products with reduced or enhanced activity. Such alterations can, for example, alter one or more of the biological functions of the SAT1 gene product. Further, such alterations can be selected so as to generate SAT1 gene products that are better suited for expression, scale up, etc. in the cells chosen.

The present invention also provides genetic constructs, plasmids, or vectors comprising modified SAT1 nucleotide sequence. The modified SAT1 gene, can be operatively linked to any expression control or regulatory sequences—sequences that control the expression of a DNA sequence when operatively linked to it—, more preferably from regulatory sequences of *C. albicans*. These expression control sequences may be used in vectors to express the nucleotide sequences of the invention. Accordingly, the invention further provides SAT expression modules that are nucleic acid molecules comprising a modified SAT1 nucleotide sequence and one or more regulatory sequences that are functional in pathogenic yeasts, more preferably in *C. albicans*. For example, the regulatory sequences may include promoter, terminator, and enhancer sequences. A promoter is located at the 5' non-coding region where RNA polymerase binds and promotes initiation of transcription. A terminator is located at the non-coding region 3' to the coding sequence which regulates transcriptional termination. An enhancer sequence is a cis-acting nucleic acid sequence that increases the utilization of a promoter. An enhancer can function in either orientation and in any location (upstream or downstream) relative to the promoter.

"Operably linked" refers to a link in which the regulatory regions and the nucleotide sequence to be expressed are joined and positioned in such a way as to permit transcription, and ultimately, translation. The precise nature of the regulatory regions needed for gene expression may vary for different yeasts. Generally, a promoter is required which is capable of binding RNA polymerase and promoting the transcription of an operably-linked nucleic sequence. Such regulatory regions may include those 5'-non-coding sequences involved with initiation of transcription and translation, such as the TATA box, capping sequence, CAAT sequence, and the like. The non-coding region 3' to the coding sequence may also be retained or replicated for its transcriptional termination regulatory sequences, such as terminators and polyadenylation sites. Two sequences of nucleic acid molecule are said to be operably linked when they are associated with each other in a manner which either permits both sequences to be transcribed onto the same RNA transcript, or permits an RNA transcript, to begin extended into the second sequence. A polycistronic transcript may thus be produced. Two or more sequences, such as a promoter and any other nucleic acid sequences are operably-linked if any transcription commencing in the promoter will produce an RNA transcript of the operably linked sequences. In order to be operably linked it is not necessary that two sequences be immediately adjacent to one another.

Figure 2A:
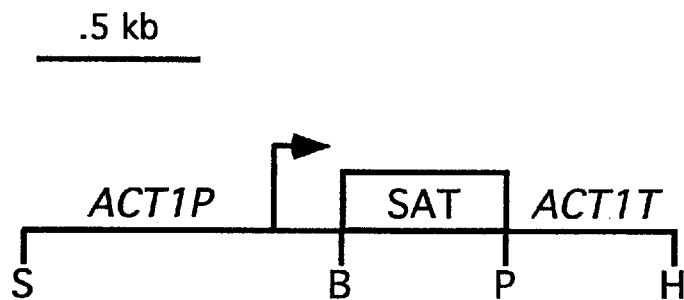

The promoter and terminator sequences for transcription are preferably derived from the genes of *C. albicans* (FIGS. 2A, B). The promoter may be constitutive or inducible. For example, in one embodiment, the promoter sequences may include 5'-non-coding sequences that interact with an inducer thus facilitating an increase or induction of gene expression of a gene product. In another embodiment, the 5'-non-coding sequences may promote constitutive expression of the gene product. In yet another embodiment, the 5'-non-coding sequences may function as an enhancer of the gene expression of a gene product. The terminator sequences may include 3'-non-coding sequences capable of inducing a response in the coding sequence. Alternatively, the 3'-non-coding sequences may facilitate constitutive expression of the coding sequence. The 3'-non-coding sequences may also contain an enhancer.

In one embodiment, the present invention provides a SAT expression module comprising the nucleotide sequence encoding the amino acid sequence of the modified SAT1 sequence (SEQ ID NO:2) operably-linked either in the 5' end, 3' end, or at both ends to the regulatory sequence(s), such that the transcription and/or translation of the SAT sequence is regulated by these sequences in a yeast cell.

Figure 2B:
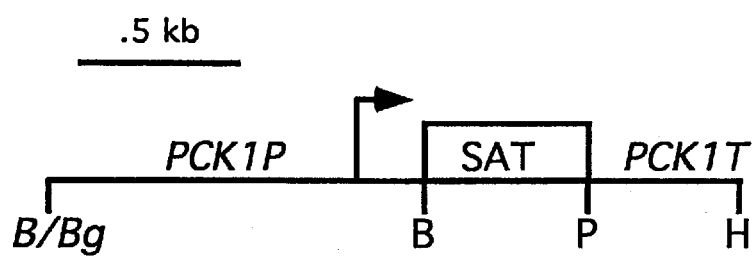

In one specific embodiment, a SAT expression module comprises a CaACT1 promoter and/or a CaPCK1 terminator sequence. CaACT1 regulatory sequence can be used to provide high constitutive expression levels of SAT1. In a specific embodiment, the SAT expression module is ASTHMA (FIG. 2A). Alternatively, since constitutive high levels of SAT1 expression may under certain circumstances produce a deleterious effect on growth rate, a CaPCK1 promoter and terminator sequences can be used to regulate SAT1 expression by growth on alternative carbon sources (Leuker et al., 1997, Gene 192:235–240). Accordingly, the present invention provides SAT expression module comprising promoter and terminator nucleic acid sequences of the CaPCK1 genes of *C. albicans* flanking the nucleotide sequences encoding the amino acid sequence of SAT1 (FIGS. 2A, B). In a specific embodiment, the SAT expression module is PSMP (FIG. 2B). In a specific embodiment, the SAT expression module is constructed on the *C. albicans* vector, pRC18 (Stoldt et al., 1997, EMBO 16:1982–1991).

Figure 2C:
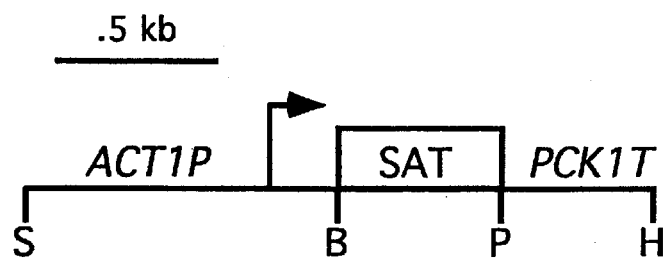

In yet another embodiment, the SAT expression module comprises a hybrid module wherein the promoter and the terminator are derived from different genes. For example, a SAT expression module is provided that comprises a nucleotide sequence of the CaACT1 promoter and a nucleotide sequence of the CaPCK1 terminator both operably linked to the coding sequence of the open reading frame of the modified SAT1 nucleic acid sequence. In a specific embodiment, the SAT expression module is ASMP (FIG. 2C). The SAT expression modules, ASTHMA and PSMP, can facilitate the targeted integration of either pRC18-ASTHMA or pRC18-PSMP into the CaLEU2 locus (creating a tandem duplication of CaLEU2 at one locus) after linearization by KpnI and transformation into CAI4 as discussed in Section 5.5.

A vector or expression construct may be used to introduce any of the above-mentioned modified SAT1 genes and SAT expression modules into a host organism for expression. The regulatory regions may be supplied by the gene that is to be expressed or the vector. A variety of vectors may be used which include, but are not limited to plasmids, cosmids, phagemids, artificial chromosomes (YACs) or modified viruses, however, the vector must be compatible with the host organism such as sequences that include but are not limited to replication origins, autonomously replicating sequences (ARS), centromere DNA, and telomere DNA. Plasmid vectors commonly in use for yeast transformation can be divided into two types: (i) replication vectors, that is those which are capable of mediating their own maintenance, independent of the chromosomal DNA of yeast, by virtue of the presence of a functional origin of DNA replication and (ii) integrating vectors, which rely upon recombination with the chromosomal DNA to facilitate replication and thus the continued maintenance of the recombinant DNA in the host cell. More specifically, in yeast, vectors include Yeast Integrating plasmids (e.g., YIp5) and Yeast Replicating plasmids (the Yrp and Yep series plasmids), Yeast centromere plasmids (the Ycp series plasmids), pGPD-2, plasmids and derivatives thereof, and improved shuttle vectors, Yiplac, Yeplac, and YCplac. (Gietz & Sugino, 1988, Gene 74:527–534). The inclusion of *E. coli* plasmid DNA sequences, such as pBR322 (Bolivar, 1978, Gene 1: 121), pBluescript or pUC19 facilitates the quantitative preparation of vector DNA in *E. coli*, and thus the efficient transformation of yeast. Preferably, the vector pRC18 is used in the present invention.

The expression vector may further contain other selectable or screenable marker genes for initially isolating, identifying or tracking host organisms that contain the gene of interest that is to be expressed. The expression vector may also provide unique or conveniently located restriction sites to allow severing and/or rearranging portions of the DNA inserts in an expression vector.

In yet another embodiment, the vector of the present invention comprises a nucleotide sequence that encodes NAT which expresses functional NAT1 in yeast, such as *C. albicans*. In another embodiment, the vector comprises a NAT expression module that expresses functional NAT1 in yeast, such as *C. albicans*.

Figure 2D:
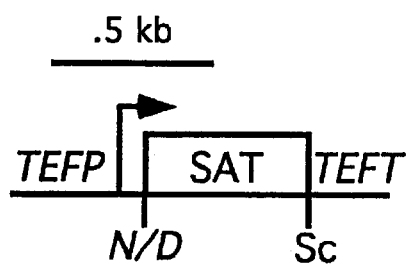

In yet another embodiment, the vector of the present invention comprises a modified KANMX4 plasmid, which comprises a modified SAT1 nucleotide sequence that expresses functional SAT1 in yeast, such as *C. albicans* and *S. cerevisiae* (Goldstein et al., 1999, Yeast 15: 1541–1553). In a specific embodiment, the entire KanR gene is replaced with the modified SAT1 open reading frame (FIG. 2D). The SAT1 expression is controlled by the TEF promoter and 3' UTR sequence. This vector can be used to transform *S. cerevisiae* such that functional SAT1 protein is expressed in *S. cerevisiae*.

The vector according to the present invention can be used in the transformation of yeast cells other than *C. albicans*, such as *S. cerevisiae* cells.

In yet another embodiment, the present invention provides organisms or cells that comprise one or more constructs, plasmids, or vectors which comprise nucleotide sequence of a modified SAT1 gene or SAT expression module. The present invention further provides organisms or cells, including yeasts, that expresses SAT1. In a preferred embodiment, the yeast is *C. albicans*. In another preferred embodiment, the yeast is *S. cerevisiae*. Pathogenic yeasts or yeast cells may be obtained from private laboratory deposits, public culture collections such as the American Type Culture Collection, from commercial supplies or primary clinical isolates. Such host organisms or cells may be further modified by techniques know in the art for specific uses.

5.3 SAT as a Dominant Selectable Marker in Eukaryotic Cells

Obtaining transformants of yeast strains requires a good method of selecting out those yeast cells which have taken up the DNA of interest. In *S. cerevisiae*, selectable marker gene (e.g. LFU2, HIS3, URA3, TRP1) complements a corresponding auxotrophic mutation in the chosen recipient. After transfection, cells are plated on (or in) a medium which does not provide the autotrophic requirement of the recipient strain. Therefore, only transformants are able to grow. However, in yeast strains where there is no autotrophic requirements, it is neither practicable nor desirable to introduce auxotrophic mutation into these strains. Therefore, transformation of some yeast strains requires the use of dominant marker genes which are selectable against a wild-type polyploid background.

The present inventors have demonstrated that both *C. albicans* and *S. cerevisiae* are sensitive to nourseothricin. The present invention provides a dominant selectable marker suitable for transformation and gene disruption experimentation in both organisms. The availability of a dominant selectable marker for experimentation in *C. albicans* improves genetic analysis in this human pathogen and offers a novel reagent pertinent to antifungal drug screening.

It has been observed that when *C. albicans* was transformed with the vector system comprising a nucleotide sequence encoding SAT1 protein according to the present invention, the vector is retained stably in the yeast and expresses functional SAT1 protein which confers resistance to NST. According to the present invention, any treptothricin/nourseothricin-resistance gene, SAT or NAT gene, may be used as a dominant selectable marker. These genes include but are not limited to the *E. coli* SAT1 and the *Streptomyces noursei* NAT1. Accordingly, the present invention provides a SAT/NST drug selection system, and a NAT/NST drug selection system which circumvents a number of obstacles in a selectable system associated with the diploid genome and asexual life cycle of *C. albicans*. Transformation of *C. albicans* using a vector comprising a modified SAT1 gene or a modified NAT gene of the present invention enables selection and stable maintenance into any *C. albicans* strain regardless of genotype. Transformants in which the vector molecule has been maintained episomally or has been integrated into the chromosome are selected efficiently using NST. As used herein, a SAT expression module that confers to a host cell normally sensitive to NST resistance to NST is referred to as a SAT dominant selectable marker.

The SAT dominant selectable marker is applicable to a broad range of eukaryotic cell types. Previously, SAT1 has been successfully demonstrated to confer nourseothricin resistance only to *Ustilago maydis* (Gold et al, 1994, Gene 142:225–230), and to the protozoan parasite, *Leishmania major* (Joshi et al., 1995, Gene 156:145–149). In the present invention, NST is utilized as a fungicide to control growth of or to kill pathogenic fungi with the proviso that the fungi is not *Ustilago maydis*. In this context, a preferred pathogenic fungi is the human opportunistic pathogen, *C. albicans*. In addition, the SAT dominant selectable marker may be used in *S. cerevisiae*. This dominant selectable marker can be adapted for use in *S. cerevisiae* which may be useful in academic research, and in pharmaceutical and brewing industries. This broad range nourseothricin sensitivity and corresponding SAT-dependent resistance, in conjunction with the drug's mechanism of disrupting the universal process of protein synthesis extends its utility to mammalian cell types and development of antibiotics.

Accordingly, the present invention provides a method for introducing recombinant DNA into yeast strains and for obtaining stable transformants. The present invention provides a method of selection for transformants comprising the steps of: a) introducing a SAT expression module into a cell; and b) growing the cell in the presence of NST. Transformed cells that express SAT1 protein can grow in the presence of NST and can thus be identified. The amount of NST used can be determined empirically by one skilled in the art, and for *C. albicans*, about 200 µg/ml is preferred.

The present invention also provides a method for transformation of yeast with a gene that encodes an identification marker wherein the identification marker is SAT1 and where the method comprises transforming yeast with a gene encoding SAT1 such that the SAT integrates into the chromosome of the yeast in a manner which permits detection of the gene and identification of the yeast, for example, following restriction digestion of the chromosome. The yeast transformed using the method of the present inventions include, for example, *C. albicans* and *S. cerevisiae*.

The present invention also provides a method for selecting a yeast which expresses SAT1 that has been transferred into the yeast by recombinant DNA techniques, such method comprises the steps of: a) operatively linking a modified SAT1 gene of the present invention in a plasmid; b) transforming the yeast with the plasmid; c) selecting a transformed yeast of step (b) which expresses SAT1 by direct selection on a medium containing NST.

When nourseothricin/streptothricin-resistance SAT gene is used as a dominant selectable marker, transformants in which a targeting vector has been integrated are selected efficiently. Constitutive expression of SAT1 by the promoter functions as a dominant selectable marker enabling direct selection of drug-resistant transformants in *C. albicans*. Instead of using direct selection for NST-resistant transformants, alternatively, selection for NST-resistant transformants can be achieved when a nonselective preincubation period is adopted, i.e., the transformants can be grown for 12–18 hr prior to selection with NST. This nonselective preincubation period enables sufficient expression of SAT1 prior to contact with the drug. Accordingly, NST-resistant transformants can be detected by employing a nonselective preincubation period.

The present invention also provides a method of selection for transformants comprising the steps of: a) introducing a vector comprising NAT1 nucleic acid into a cell; and b) growing the cell in the presence of NST. Transformed cells that express SAT1 can grow in the presence of NST and can thus be identified.

The present invention also provides a method for transformation of yeast with a gene that encodes an identification marker wherein the identification marker is NAT1 and where the method comprises transforming yeast with a modified NAT1 gene according to the present invention encoding NAT such that the modified NAT gene integrates into the chromosome of the yeast in a manner which permits detection of the gene and identification of the yeast, for example, following restriction digestion of the chromosome.

The present invention also provides a method for selecting a yeast which expresses NAT1 that has been transferred into the yeast by recombinant DNA techniques, such method comprises the steps of: a) operatively linking a modified NAT gene of the present invention in a plasmid; b) transforming the yeast with the plasmid; c) selecting a transformed yeast of step (b) which expresses NAT1 by direct selection on a medium containing NST.

Preferably, the yeast is *C. albincans* or *S. cerevisiae*. Homologs of SAT1 or NAT1 proteins, i.e., other SAT or NAT proteins, can also be used in a similar fashion.

5.4 Gene Disruption using SAT

After showing that SAT performs as a dominant selectable marker, the present inventors demonstrate the usefulness of the system in targeted gene disruption experiments. Having a dominant selectable marker for a given organism on a DNA plasmid allows for either random or targeted insertion of the selectable marker into the host genome. This is achieved by selecting for cells that have incorporated the dominant selectable marker. In some instances, the insertion may inactivate certain genes in the host. In other instances, the SAT expression module may be designed to allow precise homologous gene replacement for a particular gene in the host organism.

The gene disruption methodology of one embodiment of the present invention involves the integration of a modified SAT1 gene randomly into the genome of a host organism. In this embodiment, no target sequence is present upstream or downstream of the modified SAT1 gene. Another standard gene disruption methodology involves homologous recombination between the flanking sequence of a gene targeting vector with sequences at the desired locus. The result is that, the selectable marker can be inserted into, or replaces sequences of the target gene. The gene targeting vector of the present invention can be any vector described in Section 5.2 supra. In one embodiment, the invention provides that a modified SAT1 gene is inserted into the DNA sequences in *C. albicans* and replaces the homologous sequences on a chromosome. The vector useful for this embodiment of the present invention is a nucleic acid which comprises SAT expression modules and sequences homologous to the target DNA sequences of *C. albicans*. Preferably, the SAT expression module sequence is flanked by such sequences that are homologous to the target site in the chromosome of the organism. Accordingly, the invention provides a targeting vector that comprises a modified SAT1 gene, preferably a SAT expression module, a first nucleotide sequence and a second nucleotide sequence, wherein the first and second nucleotide sequences flank both ends of the modified SAT1 gene, and are hybridizable separately to different non-contiguous regions of a chromosome of *C. albicans* or *S. cerevisiae*. Preferably, the first and second nucleotide sequences of such a targeting vector are separately hybridizable to regions of a yeast chromosome that are contiguous with a single target gene of interest. The targeting vector is linearized by digestion at an appropriate restriction site. Upon transfection, the modified SAT1 gene integrates into the chromosome of *C. albicans* by homologous recombination.

In one embodiment, the present invention provides methods for gene disruption which are based on PCR. The vector used in this method can be any vector that comprises a SAT expression module as described above. Preferably, the flanking sequence is about 50–65 base pairs. The methods involve the amplification of a selectable marker to which flanking sequence of minimal length sufficient for homologous recombination and replacement of a target locus can occur (Baudin et al., 1993 Nucleic Acids Res. 21:2239–3330).

In a specific embodiment, the disruption vector comprises a SAT expression module that comprises promoter and terminator sequences from different genes. In a preferred embodiment, a SAT expression module comprises the CaACT1 promoter and the CaPCK1 terminator sequences to minimize the potential for homologous recombination to either locus (FIG. 2C). In a specific embodiment, gene disruption fragments are generated by PCR amplification of ASMP in which 65 base pairs of flanking sequences homologous to CaKREL, CaWSC4 or YHR036w strains was added. In the most preferred embodiment, the vector is ASMP.

Accordingly, the SAT selection system can be applied to PCR-based gene disruption experiments in *C. albicans*—including strains lacking auxotrophic markers. Gene disruption is achieved with high efficiency (65–90% depending on locus) with a minority of transformants being SAT-containing misintegrants (10–35% of drug resistant colonies). This frequency for correct integration is significantly greater than reported for PCR-based gene disruptions using a number of different auxotrophic markers in *C. albicans* (Wilson et al., 1999, J. Bact. 181:1868–1874), and ensures the likelihood of identifying the desirable mutation with minimal effort. Methods known to those skilled in the art, for example, PCR can be used to identify the integration that occurred at the desired location.

In another embodiment, the invention provides a method for making a homozygote which uses the cre recombinase system to excise a modified SAT1 gene sequence which has disrupted a gene by targeted integration within a cell. The method involves the use of *C. albicans* cells that has a regulatable expression system for cre recombinase (e.g., CaPCK1-regulatable cre recombinase), and a SAT expression module for gene disruption that comprises cre recombinase sites flanking the modified SAT1 sequence. The nucleotide sequence for the cre recombinase may, if desired, be modified for proper expression in *C. albicans*. Once the cells that have the SAT expression module are selected, the SAT expression module could be excised by activation of cre recombinase under derepressing conditions (e.g., NST plates containing 1% Casamino acid for a CaPCK-1 regulatable constuct). The resulting strain of *C. albicans* which is heterozygous with respect to a first disrupted gene is sensitive to NST, and can be re-transformed with the same PCR-based disruption construct to generate the desired homozygote. Phenotypic analysis of the resulting homozygote would be assessed under rich conditions where expression of cre recombinase is repressed (YEP plates containing 2% glucose).

Preferably, the SAT1 marker could be made reusable for generating homozygotes by constructing a gene fusion between SAT1 and a negative selectable marker gene such as thymidine kinase (TK). In this embodiment, counterselection of SAT-TK can be employed by using gancyclovir (GANC).

In yet another embodiment, the invention provides that *C. albicans* is also sensitive to a second antibiotic, blasticidin (FIG. 1; Karreman, 1998, Nuc. Acid. Res. 26:2508–2510). The invention further provides the BSR gene of *Bacillus ceraus* which confers resistance to blasticidin can be used in *C. albicans* provided that the gene is expressed resulting in the production of a functional gene product. Accordingly, expression of the bacterial BSR gene in *C. albicans* is made possible by engineering the gene so that its DNA sequence is altered to conform to the genetic code of *C. albicans*. Accordingly, the invention provides a modified BSR gene which expresses a functional BSR gene in *C. albicans*. In a specific embodiment, the invention provides a nucleic acid molecule comprising the nucleotide sequence that encode a functional BSR enzyme in *C. albicans*.

5.6 Uses of SAT in *Saccharomyces cerevisiae*

Figure 4A:
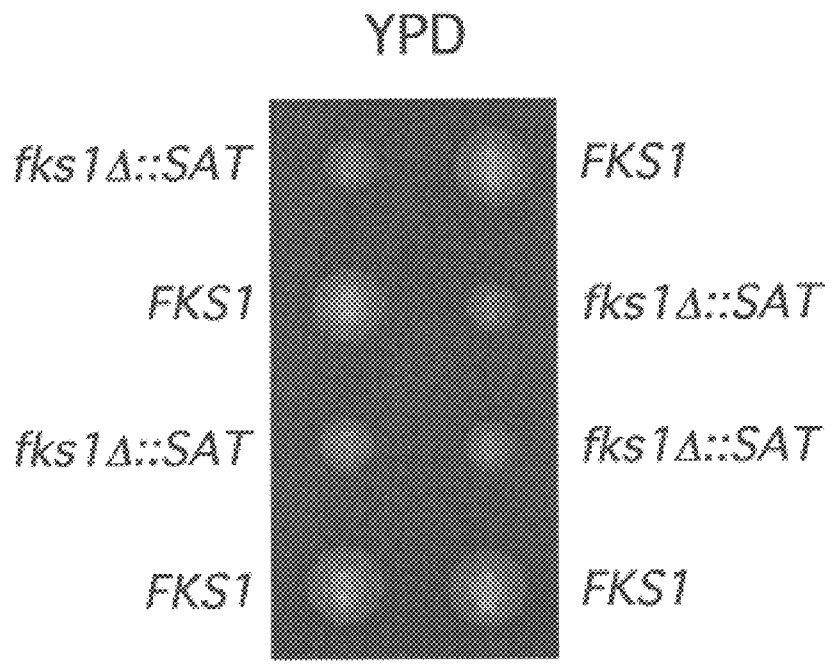
Figure 4B:
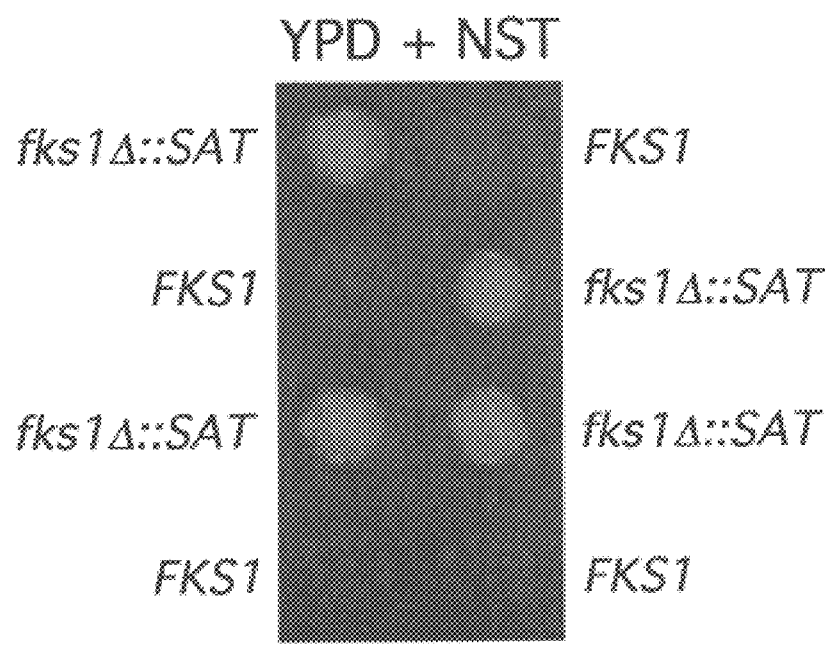

A modified KANMX4 plasmid which comprises a SAT1 nucleotide sequence that expresses functional SAT1 in yeast was constructed in which the entire KanR gene has been replaced with the complete SAT1 open reading frame (FIG. 2D). In this way, SAT1 expression is controlled by the TEF promoter and 3' UTR sequence, and can be readily amplified as a PCR fragment containing homologous flanking sequence for targeted integration into a particular genomic location. To test whether the SAT1 selectable marker functions in *S. cerevisiae*, a PCR-based gene disruption of the FKS1 gene was performed. A PCR product containing 65 bp of FKS1 5' and 3' noncoding sequence flanking the SAT expression module was transformed into the *S. cerevisiae* diploid strain SEY6210. Homologous recombination between this DNA fragment and one FKS1 allele is predicted to result in complete replacement of the FKS1 open reading frame with the SAT1 marker. Following overnight growth under non-selective conditions, replica-plating onto NST-supplemented YEPD plates gave rise to multiple NST-resistant colonies after 2 days. PCR analysis demonstrated approximately 75% of transformants examined to be FKS1/fks1D::SAT heterozygotes. Tetrad dissection of two such independently-derived NST-resistant transformants demonstrates proper disruption of one FKS1 allele using the SAT dominant selectable marker, as a 2:2 slow-growth phenotype, characteristic of fks1 null mutation (Douglas et al., 1994, Proc. Natl. Acad. Sci. 91:12907–12911), cosegregates with NST resistance with both strains examined (FIG. 4).

Accordingly, the present invention provides a nucleic acid and vector comprising a nucleotide sequence encoding SAT1 protein operably linked to a TEF promoter sequence and a 3' UTR sequence, and nucleotide sequences homologous to chromosomal sequences by *S. cerevisiae*.

The present invention also provides a *S. cerevisiae* cell comprising a nucleic acid sequence comprising a nucleotide sequence encoding SAT1 protein operably linked to a TEF promoter sequence, a 3' UTR sequence, and nucleotide sequences homologous to chromosomal sequences of *S. cerevisiae*.

The present invention also provides a method of selection for transformants comprising the steps of: a) introducing a vector comprising SAT nucleic acid into a cell; and b) growing the cell in the presence of NST.

5.6 SAT in vitro and in vivo Drug Screening Assays

SAT1 expression in *C. albicans* offers utility as a novel reporter gene applicable to both in vitro and in vivo drug screening assays. SAT1 has been biochemically demonstrated to transfer an acetyl group from acetyl-coenzyme A to an amino group of the beta-lysine (peptide) chain of streptothricin F (Zahringer et al., 1993, FEMS Microbiol Lett 110:331–334). Thus, a SAT1 activity assay employing $^{14}C$ N-acetyl coenzyme A and streptothricin F exists. Such a heterologous biochemical assay enables SAT1 activity to be monitored in complex whole cell assays, without time consuming purification or contaminating background enzymatic activity.

Alternatively, SAT1-based nourseothricin resistance could be employed in *C. albicans* or *S. cerevisiae* as a reporter gene in a whole cell assay to screen for antifungal compounds. In principle, the modified SAT1 gene of the present invention would be fused to a *C. albicans* promoter which is demonstrated to exhibit a transcriptional profile that is associated with the loss of activity of a specific drug target. Accordingly, the invention provides a *C. albicans* cell that comprises a reporter gene construct comprising a promoter that is operably linked with a modified SAT1 gene, wherein the activity of the promoter is activated or upregulated when a compound binds to or inhibit a specific drug target in the same cell. The invention further provides the use of such cells of *C. albicans* in a drug screening assay. In this assay, compounds that bind to or inhibit a specific drug target can be detected by expression or increase in expression of the modified SAT1 gene which, as a result, confers a growth advantage to the *C. albicans* cells when they are grown in the presence of different concentrations of NST. An increased growth of cells indicates that a compound may bind to and/or inhibit the activity of the drug target.

The SAT1 coding sequence can also be used in promoter-trap assays for identifying regulatory sequences, and in assays that measure the strength of promoters and enhancers in *C. albicans* or *S. cerevisiae*. Such assays using other dominant selectable markers are well known in the art. The uses of the SAT/NST system and modified SAT1 gene as a reporter gene in various assays, such as those described in Alm and Cook (Anal. Biochem. 1990, 188:245–254, which is incorporated herein by reference in its entirety) are contemplated.

5.7 Target Discovery and Validation

The utility of the SAT dominant selectable marker in gene disruption experiments offers multiple uses in antifungal drug discovery. Drug target validation by gene disruption is a standard experimental approach for predicting the suitability of a particular gene product for rational antifungal drug screening. PCR-based gene disruptions using the SAT selectable marker improves both the speed and the simplicity of target validation in *C. albicans*.

The SAT dominant selectable marker is also useful in standard antifungal drug screening practices, in which either integrative transformation or gene disruption methodologies are required. For example, a SAT1-containing integration plasmid could be directly applied to in vivo antifungal drug screens based on overexpression of a validated drug target, where, in a dosage-dependent manner, elevated levels of the gene product produce corresponding levels of drug resistance. Compounds identified by this titration effect potentially interact directly with the drug target and therefore suggest their mode of action. Moreover, overexpression screens using drug targets exclusive to fungi improves the likelihood of uncovering compounds displaying high efficacy and reduced toxicity. Reciprocally, a C. albicans strain containing a SAT-based gene disruption of a potential drug target can similarly be screened in vivo for compounds demonstrating gene deletion-correlative resistance; where resistance presumably results from elimination of the drug target. Compounds demonstrating such target-dependent activity, can then be more precisely examined for antifungal activity and potential as a therapeutic drug.

A PCR-based heterozygous strain collection derived using the SAT dominant selectable marker also offers multiple uses in antifungal drug research. Heterozygous strains often reveal intermediate phenotypes (haploinsufficiency) which is diagnostic of the phenotype associated with the homozygous null mutation. Such a collection could be used as a primary screen for genes potentially essential for viability, pathogenicity, temperature sensitivity, (or any other process relevant to antifungal drug discovery) and subsequently assessed by target validation. Incorporating a unique oligonucleotide sequence or molecular "bar code" into the SAT dominant selectable marker of each heterozygote enables drug-sensitivity profiling, or haploinsufficiency screens, to be performed in C. albicans (Giaever et al., 1999, Nature Genet. 21:278–283). Such a strain collection offers the potential to identify the target protein to both known and novel drugs.

6. EXAMPLES

6.1 Composition of Medium

The composition of a YPD medium for culturing yeast contains 1% yeast extract, 2% bactopeptone and 2% glucose. Agar was added in an amount of 2% to the medium in the case of a plate form. Transformant were selected on Ura+ protopthy and subsequently streaked onto nourseothricin-supplemented plates containing either 1% Casamino acid (derepressing conditions) or YEP containing 2% glucose (repressing conditions) as alternative carbon sources.

6.2 Transformation Method

The conventional methods of the transformation of *Candida albicans* include the protoplast method, electroporation, gene disruption and modifications thereof.

Transformants are selected for Ura+ prototrophy and streaked onto nourseothricin supplemented plates. In the preferred embodiment, the selection plates contained either 1% Casamino acid for depressing conditions or YEP with 2% glucose for repressing conditions as alternative carbon sources to control CaPCK1 dependent expression of SAT1. All pRC18-PSMP transformants tested for resistance to nourseothricin under CaPCK1 depressing conditions. Contrastly, the transformants displayed complete sensitivity to nourseothricin under conditions of CaPCK1 repression. Therefore, in the preferred embodiment, 400 µg/ml nourseothricin under depressing conditions comprising 1% Casamino acid is used to test resistance to NST.

Figure 3A:
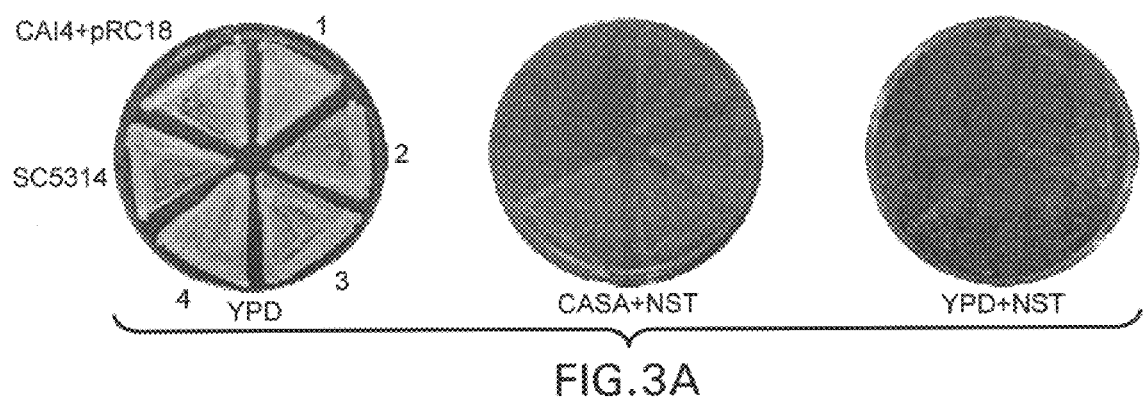

6.3 Determination of Transformation in *Candida albicans* pRC18-PSMP transformants were selected for Ura+ prototrophy and subsequently streaked onto nourseotliricin-supplemented plates containing either 1% Casamino acid (derepressing conditions) or YEP containing 2% glucose (repressing conditions) as alternative carbon sources to control CaPCK1-dependent expression of SAT1 (FIG. 3A). All pRC18-PSMP transformants tested displayed robust resistance to nourseothricin (400 µg/ml) under CaPCK1 derepressing conditions, whereas complete Nourseotliricin sensitivity was observed under of CaPCK1 repressing conditions. CAI4 maintaining only the pRC18 vector and the parent strain, SC5314, failed to grow in the presence of the drug irrespective of carbon source. This CaPCK1-dependent expression of SAT1 demonstrated resistance to nourseothricin at concentrations which otherwise would kill wild type C. albicans lacking the resistance gene.

6.4. Vectors for Gene Disruption in *C. albicans*

The targeting construct of ASTHMA module is used to disrupt the CaACT1 locus in C. albicans. The structure of the ASTHMA module is described above. Restriction digestion of the ASTHMA module from pRC18 using SmaI and HindIII generates a CaACT1 disruption fragment, comprising the CaACT1 promoter and termination sequence flanking SAT. Homologous recombination between this flanking sequence and the CaACT1 locus is predicted to result in perfect replacement of one CaACT1 allele with SAT. To test whether heterozygous CaACT1/caact1D::ASTHMA transformants could be selected directly, 10 µg of pRC18-ASTHMA was digested with SinaI and HindIII to remove ASTHMA, transformed into CAI4, and plated on YPD+NST (400 µg/ml). Of 19 transformants examined by PCR (data not shown), 15 transformants were shown to contain a correct caact1D::ASTHMA allele, (the 4 remaining strains also stably maintained ASTHMA DNA, but integrated elsewhere in the genome) demonstrating the utility of SAT1 as a dominant selectable marker in a targeted gene disruption experiment.

In a specific embodiment, the ASTHMA module is obtained from digesting pRC18 using SmaI and HindIII to generate a CaACT1 disruption fragment which comprises the SAT gene flanked by the nucleic acid sequences of the CaACT1 promoter and terminator.

Figure 3B:
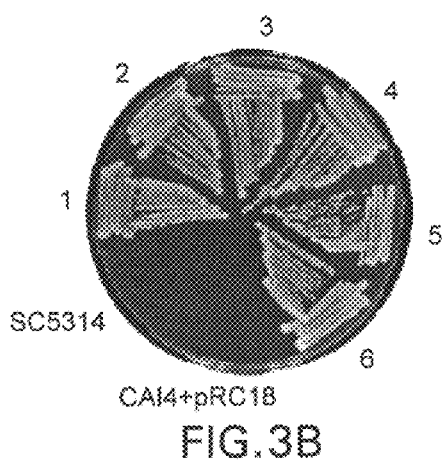

6.5 Utility of SAT as Dominant Selectable Marker pRC18-ASTHMA was linearized and transformed into CAI4 and plated iirectly on nourseothricin (400 µg/ml)-supplemented YPD plates to select for stable drug esistance. Drug resistant colonies arose at a frequency of approximately 10 per µg DNA, a relatively poor transformation efficiency compared to S. cerevisiae, but typical in C. albicans. Verification of transformants maintaining the pRC18-ASTHMA integration plasmid was determined by PCR and Southern blot analysis (FIG. 4A). Robust growth of six pRC18-ASTHMA transformants restreaked onto a YPD+nourseothricin plate versus CAI4 maintaining only pRC18 vector and the parental strain, SC5314 are shown (FIG. 3B). Thus constitutive expression of SAT1 by the CaACT1 promoter functions as a dominant selectable marker enabling direct selection of drug-resistant transformants in C. albicans. Moreover, no significant difference in growth rate, cell shape, germ tube formation or hyphal development were observed between CAI4 strains maintaining either pRC18, or pRC18-ASTHMA, suggesting that the SAT selectable marker is suitable for pathogenicity and virulence studies in a mouse model system.

6.6 Gene Disruption by PCR

To adapt SAT as a dominant selectable marker for PCR-based gene disruptions in C. albicans, a number of modifications were necessary. Because the vector ASTHMA contains substantial homologous sequence to the CaACT1 locus, and consequently is capable of mistargeting into the CaACT1 locus, a final SAT expression cassette (ASMP) was constructed in which the CaACT1 promoter and CaPCK1 termination sequence were combined to minimize the potential for homologous recombination to either locus (FIG. 2C). Gene disruption fragments were generated by PCR amplification of ASMP such that 65 bp of flanking sequence homologous to CaKRE1, CaWSC4, or YHR036w was added. Although direct selection for NST-resistant transformants proved successful in previous experiments, where substantial homologous sequence was available to facilitate stable integration, no transformants were recovered when directly selecting for PCR-amplified ASTHMA gene disruptions. Selection for NST-resistant transformants was achieved however, when a nonselective preincubation period was adopted; where transformants were first plated on YPD 12–18 hr prior to replica plating onto YPD-NST (400 µg/ml) plates. Presumably, this nonselective preincubation period enables sufficient expression of SAT1 prior to contact with the drug. Both large and small-sized colonies are detected after 48 hr growth on drug-supplemented plates. Restreaking both classes of colonies on YPD-NST reveal that only the large-sized colonies stably maintained drug resistance, allowing easy selection of bonafide transformants. Small colonies arose at a frequency of approximately $3 \times 10^{-5}$. PCR and Southern Blot analyses of the resulting transformants confirm the ASMP PCR disruption cassette targeted correctly to each locus. Moreover, heterozygous CaKRE1, CaWSC4, or YHR036w strains were identified with high efficiency. In each case, greater than 75% of large-sized transformants examined were heterozygous for the appropriate mutation within a C. albicans strain lacking any auxotrophic markers.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entireties.

What is claimed is:

1. A nucleic acid molecule comprising (a) the nucleotide sequence of SEQ ID NO: 1; or (b) a nucleotide sequence that encodes the amino acid sequence of SEQ ID NO: 2 when the nucleotide sequence is translated according to the codon usage of *Candida albicans*.

2. The nucleic acid molecule according to claim 1 which further comprises a promoter operably linked to the nucleotide sequence.

3. The nucleic acid molecule according to claim 2 which further comprises a terminator operably linked to the nucleotide sequence.

4. The nucleic acid molecule according to claim 2 or 3, where the promoter or terminator is that of the CaACT1 gene.

5. The nucleic acid molecule according to claim 2 or 3, wherein the promoter or terminator is that of the CaPCK1 gene.

6. The nucleic acid molecule according to claim 1 further comprising a nucleotide sequence encoding a negative selectable marker.

7. The nucleic acid molecule according to claim 6 wherein the negative selectable marker is thymidine kinase.

8. The nucleic acid molecule according to claim 1, 2, or 3 further comprising a first nucleotide sequence and a second nucleotide sequence, wherein the first and second nucleotide sequences flank both ends of the nucleic acid molecule, and are hybridizable separately to different non-contiguous regions of a chromosome of *Candida albicans* or *Saccharomyces cerevisiae*.

9. The nucleic acid molecule of claim 8, wherein the first and second nucleotide sequences are hybridizable to regions of a yeast chromosome that are contiguous with a gene selected from the group consisting of CaKRE1, CaWSC3, and CaYHR036W.

10. A vector comprising the nucleic acid molecule of claim 1, 2, or 3.

11. An expression vector comprising the nucleic acid of claim 2, wherein a protein displaying the activity of streptothricin acetyltransferase is expressible in *Candida albicans*.

12. A kit comprising the vector of claim 10.

13. A yeast cell comprising the nucleic acid molecule of 1, 2, or 3 wherein the yeast cell is selected from the group consisting of *Candida albicans* and *Saccharomyces cerevisiae*.

14. A yeast cell comprising a streptothricin acetyltransferase comprising the amino acid sequence of SEQ ID NO: 2 wherein the yeast cell is selected from the group consisting of *Candida albicans* and *Saccharomyces cerevisiae*.

15. A method of culturing yeast cells in the presence of nourseothricin comprising: (a) introducing the nucleic acid molecule of claim 2 into the yeast cells; and (b) culturing the yeast cells such that the nucleotide sequence of claim 2 is expressed in the yeast cells, wherein the yeast cells are cultured in a growth medium comprising nourseothricin and are cells of *Candida albicans* or *Saccharomyces cerevisiae*.

16. A method of identifying yeast cells comprising the nucleic acid molecule of claim 2, said method comprising:
   (a) introducing the nucleic acid molecule of claim 2 into the yeast cells; and
   (b) culturing the yeast cells under conditions suitable for growth and in the presence of nourseothricin for a time sufficient for the expression of the nucleotide sequence of claim 2, such that the yeast cells that contain the nucleic acid molecule grow faster than yeast cells that do not contain or express the nucleic acid molecule, thereby allowing the yeast cells that contain the nucleic acid molecule to be identified, wherein the yeast cells are cells of *Candida albicans* or *Saccharomyces cerevisiae*.

17. A method for enriching yeast cells that comprise a first nucleic acid molecule, said method comprising:
   (a) introducing a mixture of nucleic acid molecules into the yeast cells, said mixture comprising the first nucleic acid molecule and the nucleic acid molecule of claim 2;
   (b) culturing the yeast cells under growth conditions and in the presence of nourseothricin for a time sufficient for the expression of the nucleotide sequence of claim 2, such that the yeast cells that contain the nucleic acid molecule of claim 2 grow faster than yeast cells that do not contain or express the nucleic acid molecule of claim 2, thereby allowing the yeast cells that comprise the nucleic acid molecule of claim 2 to be identified; and (c) recovering the yeast cells that comprise the nucleic acid molecule of claim 2, wherein said recovered yeast cells are enriched for yeast cells that comprise the first nucleic acid molecule, wherein the yeast cells are cells of *Candida albicans* or *Saccharomyces cerevisiae*.

18. vector comprising the nucleic acid molecule of claim 8.

19. A kit comprising the vector of claim 18.

* * * * *

SEQUENCE LISTING

<160> NUMBER OF SEQ ID NOS: 2

<210> SEQ ID NO 1
<211> LENGTH: 525
<212> TYPE: DNA
<213> ORGANISM: SATI gene

<400> SEQUENCE: 1

```
atgaagattt cggtgatccc tgagcaggtg gcggaaacat tggatgctga gaaccatttc      60
attgttcgtg aagtgttcga tgtgcaccta tccgaccaag gctttgaact atctaccaga     120
agtgtgagcc cctaccggaa ggattacatc tcggatgatg actctgatga agactctgct     180
tgctatggcg cattcatcga ccaagagctt gtcgggaaga ttgaactcaa ctcaacatgg     240
aacgatctag cctctatcga acacattgtt gtgtcgcaca cgcaccgagg caaaggagtc     300
gcgcacagtc tcatcgaatt tgcgaaaaag tgggcactaa gcagacagct ccttggcata     360
cgattagaga cacaaacgaa caatgtacct gcctgcaatt tgtacgcaaa atgtggcttt     420
actctcggcg gcattgacct tttcacgtat aaaactagac ctcaagtctc gaacgaaaca     480
gcgatgtact ggtactggtt ctcgggagca caggatgacg cctaa                     525
```

<210> SEQ ID NO 2
<211> LENGTH: 174
<212> TYPE: PRT
<213> ORGANISM: SATI gene

<400> SEQUENCE: 2

```
Met Lys Ile Ser Val Ile Pro Glu Gln Val Ala Glu Thr Leu Asp Ala
1               5                   10                  15

Glu Asn His Phe Ile Val Arg Glu Val Phe Asp Val His Leu Ser Asp
```

-continued

```
                        20                  25                  30
Gly Gly Phe Glu Leu Ser Thr Arg Ser Val Ser Pro Tyr Arg Lys Asp
            35                  40                  45
Tyr Ile Ser Asp Asp Asp Ser Asp Glu Asp Ser Ala Cys Tyr Gly Ala
     50                  55                  60
Phe Ile Asp Gly Glu Leu Val Gly Lys Ile Glu Leu Asn Ser Thr Trp
65                   70                  75                  80
Asn Asp Leu Ala Ser Ile Glu His Ile Val Val Ser His Thr His Arg
                85                  90                  95
Gly Lys Gly Val Ala His Ser Leu Ile Glu Phe Ala Lys Lys Trp Ala
            100                 105                 110
Leu Ser Arg Gln Leu Leu Gly Ile Arg Leu Glu Thr Gln Thr Asn Asn
            115                 120                 125
Val Pro Ala Cys Asn Leu Tyr Ala Lys Cys Gly Phe Thr Leu Gly Gly
        130                 135                 140
Ile Asp Leu Phe Thr Tyr Lys Thr Arg Pro Gln Val Ser Asn Glu Thr
145                 150                 155                 160
Ala Met Tyr Trp Tyr Trp Phe Ser Gly Ala Gln Asp Asp Ala
                165                 170
```